United States Patent [19]

German

[11] 4,205,982
[45] Jun. 3, 1980

[54] NOBLE METAL ALLOY FOR DENTISTRY AND DENTAL RESTORATION USING SAME

[75] Inventor: Randall M. German, Avon, Conn.

[73] Assignee: The J. M. Ney Company, Bloomfield, Conn.

[21] Appl. No.: 954,343

[22] Filed: Oct. 25, 1978

[51] Int. Cl.$^2$ .............................................. C22C 5/00
[52] U.S. Cl. .................................... 75/134 N; 75/165; 75/172 G
[58] Field of Search ................ 75/134 N, 165, 172 G, 75/172 R; 32/8, 15

[56] References Cited

U.S. PATENT DOCUMENTS

| | | | |
|---|---|---|---|
| B 483,256 | 2/1976 | Tuccillo | 75/165 |
| 3,716,356 | 2/1973 | Burnett | 75/172 G |
| 4,123,262 | 10/1978 | Cascone | 75/134 N |

FOREIGN PATENT DOCUMENTS 43-8354 of 1968 Japan .......................................... 75/165

*Primary Examiner*—L. Dewayne Rutledge
*Assistant Examiner*—Peter K. Skiff

[57] ABSTRACT

A noble metal alloy having a solidus temperature above 1100° C., a Vickers hardness of at least 150 and a coefficient of thermal expansion at 600° C. of at least 0.8 percent consists essentially of 45–60 percent gold, 30–50 percent palladium and 2–7 percent tin. The alloy includes 3 to 10 percent of zinc, and mixtures thereof with indium, and up to 2 percent of rhenium, nickel, platinum and mixtures thereof. The tin to palladium ratio is 5–15:100 and the gold, palladium and platinum content must not exceed 95 percent of the composition. This alloy provides a desirable casting upon which may be fired a porcelain coating to provide a desirable dental restoration from the standpoints of hardness, inertness and aesthetics.

5 Claims, No Drawings

4,205,982

NOBLE METAL ALLOY FOR DENTISTRY AND DENTAL RESTORATION USING SAME

BACKGROUND OF THE INVENTION

Noble metal alloys are widely employed in dentistry and other applications where inertness to the environment is essential or where other characteristics provided thereby are desirable. In the production of dental restorations, gold and platinum alloys have been preferred because they exhibit desirable properties during casting and hardening, and various porcelains have been developed for use therewith to provide the desired wear properties and aesthetic appearance.

As a result, it has been generally essential to use noble metal alloys which exhibit a high solidus temperature so as to resist deformation during the firing of the porcelain coating thereon and which will also exhibit a high hardness sufficient to resist impacts upon the face and pressures occurring during mastication of foods and the like.

Unfortunately, many of the gold alloys which are available either exhibit low melting points which create problems during the firing of the porcelain coating, or excessively high costs. Moreover, some gold alloys exhibit excessive yellow coloration so as to require special opaque porcelain compositions to mask the yellowness of the casting. In order to effect optimum bonding of the porcelain coating to the noble metal alloy casting, it is generally desirable that the casting have an oxide coating which will permit the porcelain coating to bond thereto through diffusion.

Palladium has been proposed and utilized in a number of alloys with gold to increase the solidus temperature but frequently excessively lowers the thermal expansion of the alloy so that it is no longer compatible with many dental porcelains. Moreover, substantial problems are frequently encountered with gold/palladium alloys from the standpoint of achieving the necessary hardness for dental applications and from the standpoint of obtaining a casting to which the porcelain coating may be readily bonded. This is particularly true with porcelains which are based upon feldspar and nepheline syenite.

It is an object of the present invention to provide a novel noble metal alloy for dental and other applications which is substantially inert and which exhibits both high hardness and a relatively high solidus temperature.

Another object is to provide such an alloy exhibiting a thermal expansion coefficient approximating that of a wide range of porcelain materials so that it will form a desirable substrate therefor in the manufacture of dental restorations.

Still another object is to provide such an alloy wherein a porcelain coating may be bonded thereto by diffusion to provide a rugged dental restoration.

A further object is to provide rugged and attractive dental restoration utilizing an inert, hard noble metal alloy and a porcelain coating which is firmly bonded thereto.

SUMMARY OF THE INVENTION

It has now been found that the foregoing and related objects may be readily attained in a noble metal alloy consisting essentially of about 45.0–60.0 percent gold, about 30.0–50.0 percent palladium, about 2.0–7.0 percent tin, and up to 12.0 percent of optional alloying elements. The other elements comprise 3.0 to 10.0 percent of an oxidizing agent selected from the group consisting of zinc, and mixtures thereof with indium, the zinc comprising at least 3.0 percent and up to 2.0 percent of grain refiners selected from the group consisting of rhenium, nickel, platinum and mixtures thereof. The ratio of tin to palladium is within the range of 5–15:100 and the total amount of gold, palladium and platinum comprises not more than 95.0 percent of the alloy composition.

Preferably, the ratio of tin of palladium is 8–12:100, and the alloy contains 0.05–2.0 percent of the grain refining component and 3.0–9.0 percent of the oxidizing agent component. The gold is present in an amount of 48.0–56.0 percent and the palladium is present in the amount of 34.0–40.0 percent.

In accordance with the invention, the casting produced from the above alloy has a solidus temperature above 1100° C., a Vickers hardness of at least 150 and a coefficient of thermal expansion at 600° C. of at least 0.8 percent. A porcelain coating is provided upon at least a portion of the casting and firmly bonded thereto to provide a dental restoration. Since a thin oxide layer is present upon the surface of the casting, the coating is bonded thereto by diffusion.

DETAILED DESCRIPTION OF THE PREFERRED EMBODIMENTS

As previously indicated, the essential components of the alloy are gold, palladium and tin with zinc or indium and zinc as an oxidizing component and platinum, nickel and rhenium as optional grain refining components. Small amounts of other non-interfering metals may be present although they are not essential and may be deleterious to the composition.

As previously indicated, the gold content may vary from as little as 45.0 to as much as 60.0 percent. Below 45.0 percent, the thermal expansion coefficient is too low for most applications and the nobility or inertness of the alloy is reduced from the standpoint of preventing tarnish, corrosion and tissue reactions. If the gold content exceeds 60 percent, the alloy becomes too soft for many dental applications. The preferred alloys contain about 48.0–56.0 percent with the optimum being 50.0–54.0 percent.

The palladium content may vary from 30.0–50.0 percent with the preferred formulations containing 34.0–40.0 percent and optimally 36.0–39.0 percent. The palladium maintains high nobility in the alloy for biocompatability and provides one component of the hardening mechanism. In addition, it beneficially lowers the alloy density and maintains the desired nobility at a lower cost. Above about 50.0 percent, the thermal expansion coefficient is excessively reduced from the standpoint of compatability with dental porcelains. Below about 30.0 percent, hardening is insufficient.

The noble metal content of the alloy will equal at least 81.0 percent of the alloy and will preferably be on the order of 86.0–93.0 percent. It should not exceed 95.0 percent since hardness is excessively reduced.

Tin is an essential element of the composition since it cooperates with the palladium to provide the hardening mechanism and it additionally provides means for diffusion bonding of the porcelain to the alloy. Although it may range from 2.0–7.0 percent and within a ratio to palladium of 5–15:100, it preferably is within the range of 3.0–6.0 percent and the ratio of 8–12:100. Below about 2.0 percent, there is insufficient hardening; above 7.0 percent, there is a tendency to produce a brittle, two-phase alloy.

The optional components include grain refining components selected from the group consisting of rhenium, platinum, nickel, and mixtures thereof. This component also has some beneficial effect upon hardening but should not exceed about 2.0 percent. Grain refinement for dental casting alloys is desirable from the standpoint of mechanical properties although not essential. Of the several elements, small amounts of rhenium have been preferred and as little as 0.05 percent, and even less, is beneficial.

The remaining component comprises oxidizing agents selected from the group consisting of zinc, and mixtures thereof with indium. They also have some beneficial effect upon hardness but should not exceed about 10.0 percent because they will adversely affect nobility of the alloy and other properties. These elements are advantageous in that they provide deoxidizing action for the alloy and thereby prevent bubbling of the porcelain during firing and they also passivate the surface of the alloy against reactions with the investment material. As oxidizable metals, they provide a thin oxide coating on the alloy casting which promotes bonding with the porcelain cast thereagainst. Although zinc may be used singly in amounts of 3.0-9.0 percent, it is preferably used in combination with indium within this range and most desirably at about 6.5-8.0 percent.

The alloys of this invention may be cast readily to provide cast structures with a good thermal expansion coefficient, good hardness and high nobility. Temperatures of about 1300° C. are desirable for the casting operation since the solidus temperature is about 1200° C.; cooling may be effected in any manner since the alloy is not age hardening. The normal casting procedures generate a thin oxide coating which is beneficial from the standpoint of promoting bonding of the porcelain thereto. The porcelain composition can be fired against the casting at any suitable temperature for the porcelain since the alloy is not age hardening.

Since the alloy has a tendency to absorb gas during casting, it is generally desirable to degas the castings before firing the porcelain coatings thereon to avoid blistering, etc. Degassing is accomplished rapidly under vacuum conditions with optimum conditions being at about 500-720 mm. Hg. The castings are rapidly heated from about 600° to 1200° C. at rates of about 40°-65° C. per minute, and then removed and cooled slowly, preferably under glass.

Illustrative of the efficacy of the alloys of the present invention are the following data wherein the results of varying the amounts of the various essential and optimum components are reported.

| Alloy No. | \multicolumn{6}{c}{Alloy Elements, weight percent} | | | | | | Properties | | |
|---|---|---|---|---|---|---|---|---|---|
| | Sn | Au | Pd | In | Zn | Other | Vickers Hardness | Thermal Expansion % at 600° C. | Sag Temp °C. |
| 1 | 0.0 | 55.0 | 36.0 | 7.0 | 1.0 | 0.9 Pt, 0.1 Re | 103 | 0.819 | 1330 |
| 2 | 1.5 | 50.0 | 44.4 | 4.0 | — | 0.1 Re | 126 | 0.770 | 1360 |
| 3 | 1.5 | 50.0 | 43.4 | 5.0 | — | 0.1 Re | 124 | 0.779 | 1345 |
| 4 | 2.5 | 50.0 | 39.0 | 8.0 | — | 0.5 Re | 263 | 0.821 | 1300 |
| 5 | 2.5 | 50.0 | 39.4 | 8.0 | — | 0.1 Re | 216 | 0.833 | 1300 |
| 6 | 2.5 | 50.0 | 38.4 | 9.0 | — | 0.1 Re | 229 | 0.825 | 1290 |
| 7 | 2.5 | 50.0 | 38.5 | 8.0 | 1.0 | — | 245 | 0.843 | 1290 |
| 8 | 3.0 | 49.7 | 41.3 | 2.9 | 3.0 | 0.1 Re | 166 | 0.825 | 1260 |
| 9 | 3.4 | 52.0 | 37.4 | 3.3 | 3.8 | 0.1 Re | 257 | 0.841 | 1250 |
| 10 | 3.5 | 50.0 | 40.5 | 3.0 | 3.0 | — | 190 | 0.827 | 1315 |
| 11 | 3.6 | 49.3 | 40.8 | 3.1 | 3.2 | — | 258 | 0.809 | 1300 |
| 12 | 4.0 | 52.0 | 39.0 | 7.0 | — | — | 223 | 0.802 | 1285 |
| 13 | 4.0 | 50.0 | 38.0 | 7.0 | — | 1.0 Ni | 262 | 0.849 | 1260 |
| 14 | 4.0 | 53.0 | 35.9 | 7.0 | — | 0.1 Re | 246 | 0.805 | 1270 |
| 15 | 4.0 | 52.0 | 38.0 | 6.0 | — | — | 154 | 0.802 | 1290 |
| 16 | 4.5 | 50.0 | 40.9 | 4.5 | — | 0.1 Re | 226 | 0.811 | 1300 |
| 17 | 5.0 | 54.0 | 40.0 | — | — | 0.9 Pt, 0.1 Re | 265 | 0.829 | 1260 |
| 18 | 5.2 | 57.0 | 36.9 | — | — | 0.8 Pt, 0.1 Re | 267 | 0.825 | 1340 |
| 19 | 5.4 | 49.4 | 36.9 | 4.6 | 3.7 | — | 258 | 0.839 | 1330 |
| 20 | 6.0 | 53.0 | 37.9 | 3.0 | — | 0.1 Re | 255 | 0.815 | 1325 |
| 21 | 4.3 | 57.1 | 37.5 | — | — | 1.0 Pt, 0.1 Re | 131 | 0.823 | 1420 |
| 22 | 4.8 | 57.0 | 37.0 | — | — | 1.1 Pt, 0.1 Re | 133 | 0.828 | 1420 |

As can be seen from Alloy No. 1 in the foregoing table, the omission of tin provides an alloy with a hardness below 150 on the Vickers scale which is considered the minimum acceptable value. Alloy Nos. 2 and 3 show that tin additions below the minimum level of 2 percent also fail to meet the required minimum hardness criteria. Alloy Nos. 4-20 show variations in the amount of essential and optional additives within the scope of the present invention and all fall within acceptable levels of hardness in excess of 150 on the Vickers scale, of thermal expansion above 0.8 percent of 600° C. and of sag temperatures of at least 1200° C. to permit porcelain firing.

Of the variations shown in Alloy Nos. 4-20, Alloy Nos. 4 and 5 show the effect of increasing the amount of the grain refiner rhenium. Alloy Nos. 4-6 show the effect of increasing indium content while Alloy Nos. 7-11 show the use of bath indium and zinc as oxidizers in varying amounts while varying the tin content. Alloy Nos. 12-14 use a higher tin content and show the effect of including nickel or rhenium as a grain refining agent. Alloy Nos. 15 and 16 vary the amounts of the three essential components while Alloy Nos. 17 and 18 show the results when zinc and indium are omitted. Alloy Nos. 19 and 20 show higher tin contents. Alloy Nos. 21 and 22 show that total noble metal contents of 95.6 and 95.1 respectively are not hardened above the 150 Vickers level.

EXAMPLE

An alloy was prepared having a composition of 52.0 percent gold, 37.45 percent palladium, 3.4 percent tin, 3.8 percent zinc, 3.3 percent indium and 0.05 percent rhenium. Casting temperatures of 1427° C. are used and the castings were air cooled. This alloy was found to have a Vickers hardness of 254, a sag temperature of 1290° C. and a thermal expansion at 600° C. of 0.831. Tensile specimens prepared from the alloy exhibited a proportional yield strength of 3094 kg./cm.$^2$ and ultimate tensile strength of 7663 kg./cm.$^2$. The tensile elongation was 25% and the modulus of elasticity was 1,265,500 kg./cm.$^2$. A cylinder cast from the alloy was found to have a density of 14.2 gm./cm.$^2$.

Cylinders produced from the alloy were degassed by placing them in a muffle furnace maintained at a vacuum of 680 mm. Hg and heating them from 650° C. to 982° C. at 55° C. per minute, after which they were removed immediately and slow cooled under glass.

Onto a first cylinder was fired a nepheline syenite-based porcelain sold by The J. M. Ney Company of Bloomfield, Connecticut, bearing the designation "Opaque D104-A1 Body B0104-66" to produce a cylindrical coating of about 3 mm. thickness and about 1-3 mm. in length. A firing temperature of 982° C. was employed. The shear strength of the bond was found to be 914 kg./cm.$^2$.

A similar porcelain coating was prepared using a feldspar-based porcelain produced by Dentsply International, Inc. and sold under the designation "BIOBOND Opaque 801-08 Body 738-66" at a firing temperature of 954° C. The appearance of the coating was excellent as was the strength of the bond.

A similar porcelain coating was prepared using another feldspar-based porcelain sold by Ceramco, Inc., division of Johnson and Johnson, under the designation "CERAMCO opaque 2421-66 Body 2566-66". A firing temperature of 982° C. was employed. The appearance of the coating was highly satisfactory and the bond was found to be excellent.

Thus, it can be seen that the alloy of the present invention provides a readily castable copmpostion for use in the manufacture of dental restorations and for other applications where inertness, hardness and coefficients of thermal expansion compatible with those of porcelains are desired. The alloy is not age hardening and therefore is relatively simple to use to obtain desirable composite structures.

Having thus described the invention I claim:

1. A noble metal alloy for dental and other applications consisting essentially of:
   A. about 45.0–60.0 percent gold;
   B. about 30.0–50.0 percent palladium;
   C. about 2.0–7.0 percent tin;
   D. about 3.0–10.0 percent of oxidizing component selected from the group consisting of zinc and mixtures thereof with indium, said oxidizing component containing at least 3.0 per cent zinc; and
   E. about 0.0–2.0 percent of grain refining component selected from the group consisting of rhenium, nickel and platinum and mixtures thereof; all based upon the total weight of the alloy, the ratio of tin to palladium being 5–15:100 and the total amount of gold, palladium and platinum comprising not more than 95.0 percent of the alloy.

2. The alloy of claim 1 wherein said ratio of tin to palladium is 8–12:100.

3. The alloy of claim 1 wherein said alloy contains 0.05–2.0 percent of grain refining component.

4. The alloy of claim 1 wherein said gold is present in the amount of 48.0–56.0 percent, said palladium is present in the amount of 34.0–40.0 percent and said ratio of tin to palladium is 8–12:100.

5. The alloy of claim 4 wherein said alloy contains 0.05–2.0 percent of grain refining component.

* * * * *